United States Patent [19]

Koutrakis et al.

[11] Patent Number: 5,185,129

[45] Date of Patent: Feb. 9, 1993

[54] OZONE MONITORS

[75] Inventors: Petros Koutrakis, Cambridge; Jack M. Wolfson, Jamaica Plain, both of Mass.

[73] Assignee: President and Fellows of Harvard College, Cambridge, Mass.

[21] Appl. No.: 662,164

[22] Filed: Feb. 28, 1991

[51] Int. Cl.$^5$ ............................................. G01N 31/22
[52] U.S. Cl. ...................................... 422/88; 422/83; 422/90; 436/902
[58] Field of Search ...................... 436/1, 79, 110, 135, 436/150, 902, 904; 422/78, 68.1, 88, 83, 90

[56] References Cited

U.S. PATENT DOCUMENTS

| | | | |
|---|---|---|---|
| 3,528,779 | 9/1970 | Fontijn | 436/135 |
| 3,888,754 | 6/1975 | Tiefensu | 204/195 R |
| 3,985,017 | 10/1976 | Goldsmith | 422/83 X |
| 3,996,005 | 12/1976 | Topol | 436/135 X |
| 4,122,032 | 10/1978 | Hollerich | 252/321 |
| 4,183,728 | 1/1980 | Leitzke et al. | 436/135 |
| 4,240,799 | 12/1980 | Ryerson | 436/135 |
| 4,849,178 | 7/1989 | Azuma | 436/135 X |

FOREIGN PATENT DOCUMENTS

| | | |
|---|---|---|
| 126109 | 6/1977 | Fed. Rep. of Germany . |
| 48-058892 | 11/1973 | Japan . |
| 0129752 | 10/1980 | Japan ..................... 436/135 |
| 0823274 | 4/1981 | U.S.S.R. ................ 436/135 |
| 862901 | 9/1981 | U.S.S.R. . |
| 902708 | 2/1982 | U.S.S.R. . |

OTHER PUBLICATIONS

"The Merck Index" Tenth Edition, Merck & Co., Inc. (1983), p. 1238, No. 8486.

Primary Examiner—James C. Housel
Assistant Examiner—Jeffrey R. Snay
Attorney, Agent, or Firm—Lyon & Lyon

[57] ABSTRACT

An ozone monitor including an ozone reactive surface, held within a container, which is adapted to specifically react with ozone. The surface is also adapted to fail to react with nitrogen dioxide in an amount which affects ozone quantitation by more than 20% when the nitrogen dioxide is provided at a concentration of 76 ppb and ozone is provided at a concentration of 30 ppb within a test gas.

17 Claims, 5 Drawing Sheets

OZONE MONITORS

BACKGROUND OF THE INVENTION

This invention relates to ozone monitors.

Ozone is an atmospheric oxidant formed through photochemical reactions of volatile organic compounds and nitrogen oxides. Daily maximum outdoor 1-hour ozone concentrations can range between 50 and 300 parts per billion (ppb), and often exceed the ozone National Ambient Air Quality Standard of 120 ppb. A large fraction of outdoor ozone may penetrate houses and other buildings (Weschler et al., *Journal of Air and Waste Management Association, JAPCA,* 39:1567–1568, 1989). High ambient levels of ozone can cause human respiratory health effects, including changes in lung capacity, flow resistance, and epithelial permeability (Lippman, *Journal of Air and Waste Management Association,* 39:672, 1989).

Suzuki et al., Taiki Osen Gakkaishi 18:544–50, 1983; Rukavishni et al., Soviet Patent Applications 902708, 1982, and 862901, 1981; Ronnebeck, German Patent Application 126109, 1977 and 1980; Tiefenau, U.S. Pat. No. 3,888,754, 1975; and Toya Rika Instruments, Japanese patent application 48058892, 1971 describe ozone gas measurement using a potassium iodide solution.

Ozone can be continuously monitored by a UV photometer where the UV absorption by ozone is determined. The greater the UV absorption, the greater the concentration of ozone.

SUMMARY OF THE INVENTION

This invention provides an air monitoring device which allows for the measurement of individual human exposure to ozone. The monitors are insensitive to other oxidants present in a normal gaseous atmosphere. They are also insensitive to the humidity and temperature of the gaseous atmospheres. The monitors of the present invention can be formed as integrated sampling monitors utilizing active or passive air sampling techniques or as a continuous monitor. These monitors are inexpensive and provide an accuracy of measurement comparable to the standard UV photometric ozone analyzer. Unlike the UV photometer, the integrated sampling monitors are simple to manufacture and suitable for both fixed area and personal monitoring. Unlike the potassium iodide monitors, they are not sensitive to sunlight, and are therefore easier to handle and use. That is, exposure of the monitor to sunlight does not significantly (i.e., ±10%) alter the value for ozone concentration obtained by use of the monitor.

Generally, the integrated sampling monitors of this invention are provided as devices containing filters coated to react specifically with ozone in a gaseous atmosphere. The coating solution used to coat the filters is a mixture of inorganic salts including nitrite ions. During the sample collection period, ozone in the sampled gas oxidizes the nitrite on the filter to nitrate. The average ozone concentration for the sampling period is determined by the amount of nitrate formed on the filter, as determined by ion chromatography or other quantitative nitrate analyzing technique. Generally, in a continuous monitor of this invention the equivalent of the coating solution is exposed to the sampled gas and nitrate is continuously analyzed in the solution.

Thus, in a first aspect, the invention features an ozone monitor having an ozone absorbing surface held within a container. The ozone absorbing surface is adapted to specifically absorb ozone without absorbing nitrogen dioxide in an amount which affects ozone quantitation by more than 20% (e.g., when nitrogen dioxide is present at a concentration of 76 ppb, and ozone at a concentration of 30 ppb within a test gas). By "absorbing surface" is meant a surface which chemically reacts with the ozone to form a product which specifically indicates that ozone had contacted the monitor surface. For example, nitrite in the surface reacts with ozone to form nitrate.

In preferred embodiments, the ozone absorbing surface is also adapted to allow accurate quantitation of ozone (within 20%, i.e., the true value ±20% of that value) at temperatures between +50° F. and +100° F., and at humidities between 10% and 90%; the surface includes a chemical coating which absorbs and chemically reacts with ozone, most preferably, the chemical coating includes nitrite ions (e.g., provided as sodium nitrite) which will react with ozone to form nitrate ions, and the coating has less than 0.1%, more preferably less then 0.03%, even more preferably less than 0.003% (by weight) nitrate ion prior to ozone exposure.

In other preferred embodiments, the chemical coating also includes a basic compound, e.g., a carbonate, such as potassium carbonate; the chemical coating also includes a hygroscopic component, e.g., glycerol; the surface is a solid surface, e.g., a filter, and the filter is held within a container adapted to be fixedly positioned to a stationary object or to the outer clothing of a person; the container envelops the filter and includes openings to allow gas to contact the filter; and the monitor is provided with a fan or pump to actively cause gas to contact the filter.

Alternately, the ozone absorbing surface is a liquid and the container is adapted to allow gaseous contact with the liquid; and the container has a gas permeable membrane, e.g. a teflon filter, which contacts the liquid and allows gas, but not liquid, to pass through the membrane. Preferably, the liquid includes nitrite, and a nitrate monitor is provided in the liquid to continuously monitor nitrate concentration as a measure of ozone in the atmosphere contacting the liquid.

Most preferably, the ozone monitor includes an ozone absorbing surface containing sodium nitrite, potassium carbonate, and glycerol.

In a second related aspect, the invention features a method for monitoring ozone in a sample of gas. The method includes providing an ozone absorbing surface adapted to specifically react with ozone, as described above; contacting the surface with the sample of gas for a measured time period; and measuring the amount of ozone absorbed by the surface.

In preferred embodiments, the surface is provided within a monitor, such as those described above, and the measuring step involves determining the amount of nitrate ions on the surface, e.g., by ion chromatography; and comparing the amount of nitrate ions on the surface to the amount of nitrate ions on the surface prior to contact with the sampled gas.

In a third related aspect, the invention features a composition adapted for the measurement of ozone. The composition includes nitrite ions, a basic component, and a hygroscopic component.

In preferred embodiments, the nitrite ion is provided as an inorganic salt, most preferably an alkali metal nitrite, e.g., sodium or potassium nitrite; the base is a carbonate, e.g., an alkaline metal carbonate, such as sodium or potassium carbonate; the hygroscopic component is glycerol; and the nitrite ion and base are provided in crystalline form.

In a fourth related aspect, the invention features a method for monitoring ozone, including the steps of providing an ozone absorbing surface including sodium nitrite, potassium carbonate, and glycerol; contacting the surface with a sample of gas for a measured period of time; and measuring the amount of ozone absorbed to the surface.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

STRUCTURE

Figure 1A:
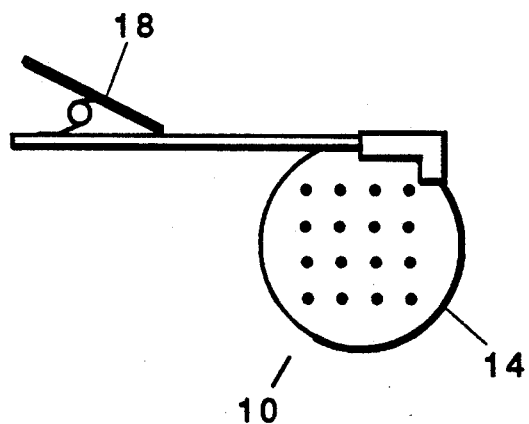
FIGS. 1A and 1B are a diagrammatic side and exploded views of a passive integrated sampler of the invention.
Figure 1B:
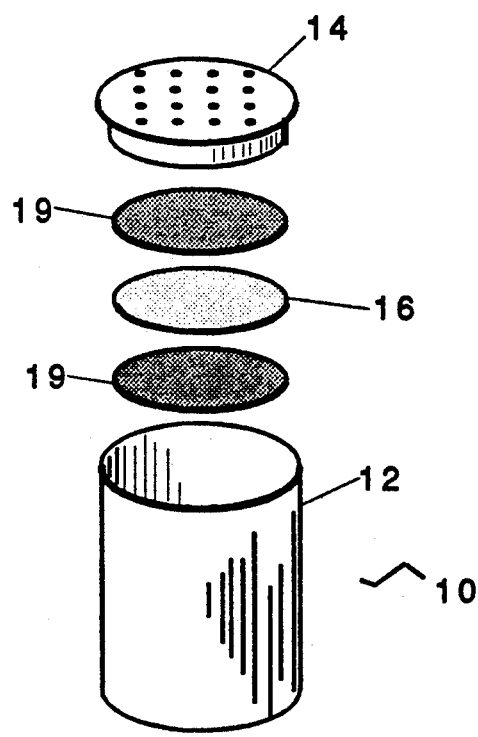

Referring to FIGS. 1A and B, a sampler 10 is formed from a container 12 having an air inlet grid 14 and a coated filter 16 having a nitrite coating. Also provided is a clip 18 to allow sampler 10 to be attached to a stationary object or to the clothing of a person. In this design, coated filter 16 is sandwiched between two wire screens 19.

Sampler 10 essentially consists of a nitrite coated glass fiber filter 16. The coating solution includes sodium nitrite (1% w/v), potassium carbonate (1% w/v) and glycerol (2% v/v) in a solvent of 70% ultrapure water and 30% methanol.

The sodium nitrite used in the coating is provided as extremely pure sodium nitrite crystals. For example, the nitrite may be obtained by standard recrystallization of ACS Certified, Baker Analyzed reagent grade sodium nitrite by heating a supersaturated solution of sodium nitrite in water at 90° C., then allow slow crystal growth as the solution cools, finally collect the resulting crystals by vacuum filtration. This recrystallization may be performed three or four times until the level of sodium nitrate within the remaining crystals is less than 0.003% (by weight). This level may be determined by making a sample of the coating solution and having it tested by ion chromatography (or by equivalent methodology).

The purified sodium nitrite is weighed to 1% (w/v) of the desired volume of coating solution to be made. Also, 1% (w/v) of analytical reagent grade anhydrous potassium carbonate is added, along with 2% (v/v) anhydrous glycerol. The remaining liquid volume is made up from a solution of 70% ultrapure water, e.g., MILLIPORE Systems, and 30% analytical reagent grade methanol. The resulting mixture is a coating solution which may be stored for several weeks at 4° C.

It is preferred to use a nitrite and carbonate in the coating solution which has sodium as the cation for one and potassium for the other. Ozone reacts more efficiently with nitrite when the nitrite and the carbonate come from salts of different metals. This may be because the mixed potassium-sodium crystals formed on the coated surface are more hygroscopic than potassium-potassium or sodium-sodium crystals. An increase in the number of water molecules in the coated surface enhances the oxidation of nitrite to nitrate by ozone. For this reason the hygroscopic compound glycerol is provided in the coating solution.

Filter 16 is prepared as a 14 mm glass fiber filter (Schleicher and Schuell grade #30; other sizes can be used, e.g., 17-25 mm, and can be formed of acid-washed cellulose or other inert material) which has been cleaned with hydrochloric acid, chromic acid, nitric acid, sodium hydroxide and methanol, and then allowed to dry. Specifically, 150 ml of concentrated nitric acid is placed into a 600 ml beaker. 100 filters are placed into the acid and carefully separated from each other. The filters remain in the acid for two hours with periodic swirling of the filters in the beaker. The acid is then decanted, and approximately 250 ml of ultrapure water added to the beaker. The filters are swirled in the water for 2-3 minutes. The water is then decanted and the water rinse procedure is repeated two more times. This procedure is repeated with concentrated chromic acid for one hour; concentrated hydrochloric acid for 0.5 hour; and 10N sodium hydroxide for 1 hour with ultrapure water rinses between each treatment. Afterwards, the filters are washed twice with ultrapure water. Finally, 25 of the filters are placed in a Buchner funnel with a light vacuum applied. The filters are then rinsed with approximately 1 liter of ultrapure water or until the pH of the residual water is neutral, as measured by pH indicator paper. 50 ml of methanol is then poured onto the filters and the filters are allowed to dry as the methanol is gently sucked through the Buchner funnel and filters. The funnel is covered with a clean tissue as the filters dry. When completely dry (approximately 20-30 minutes) the filters are stored in a clean, dry container.

0.100±0.002 ml of the coating solution is placed on the center of each of the above filters. This coating procedure is performed within a glove box under clean, dry air conditions. The coating solution disperses itself over the filter and is allowed to dry for one to two hours in the pure atmosphere of the glove box. The coated filters are then stored in clean, airtight vials until used. Filters which are not exposed to a gas sample are used to check background levels of nitrate on the filters (see below).

Prior to use, filter 16 is placed within container 12 and the container placed within a clean, airtight bottle until ready for sampling (to prevent atmospheric gases contacting the filter before ozone sampling). The sampler device is then removed from the sealed bottle and exposed to a selected gaseous environment for a measured period of time, typically one to seven days. When the filter is used for active air sampling, that is, air is mechanically forced through the coated filter, then accurate samples may be taken as low as 30 minutes. Generally, the minimum and maximum flow rates for an active sampler of this invention are 0.2 and 1 liter per minute, respectively. During the sampling period, the nitrite within the coating solution on the filter is oxidized by ozone present in the sampled gas to nitrate. It is this nitrate which is assayed as a measure of the amount of ozone in the sampled gas. Since this reaction is pH-dependent and its rate constant increases with pH, the basic compound, sodium carbonate, is used in the coating solution to keep the collecting medium alkaline. Furthermore, since the oxidation of nitrite by hydrogen peroxide is fast only at low pH, the sampling technique is insensitive to the presence of hydrogen peroxide in the sampled gas. Laboratory experiments indicate that the method is also insensitive to the presence of nitrogen dioxide (another important oxidant) in the sampled gas.

After sampling, the filter is placed into a closed container and the nitrate on the filter is extracted with 5 ml of deionized distilled ultrapure water and sonicated. (A control filter (i.e., a filter not exposed to the sampled gas and from the same batch of filters as that used for sampling, is simultaneously tested for nitrate.) Next, the extract is filtered to remove any fibrous material, then it is analyzed by ion chromatography for the concentration of nitrate. Ion chromatography analysis is performed on a Dionex 2000i instrument. An AG4A guard and AS4A separation column is used at a flow rate of 1.7 ml per minute with a detection range of 10 uS. The eluent is 1.8 mM sodium carbonate and 1.7 mM sodium bicarbonate with a regenerate of 40 mN sulfuric acid.

The amount of nitrate in the extract determined by ion chromatography, or other quantitative technique, allows direct measurement of the ozone present in the sampled gas. The number of moles of ozone collected by the coated filter medium is equal to the number of moles of nitrate formed. Of course, nitric acid gas and nitrate particles collected simultaneously on the alkaline filter medium during ozone sampling may affect the measurement. However, under usual ambient conditions this positive interference represents less than 5% of the nitrate formed during the nitrite ozone reaction. Alternately, reaction of the ozone with organic aerosols collected on the filter media can result in an underestimation of ozone concentration. However, due to the amount of nitrite on the coated filter relative to expected concentrations of organic aerosols, this interference is thought to be relatively small.

Figure 2A:
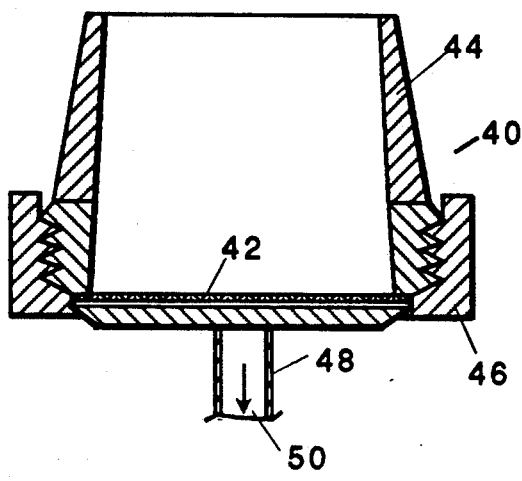
FIGS. 2A and 2B are diagrammatic cross-sectional and top views of an active integrated sampler.
Figure 2B:
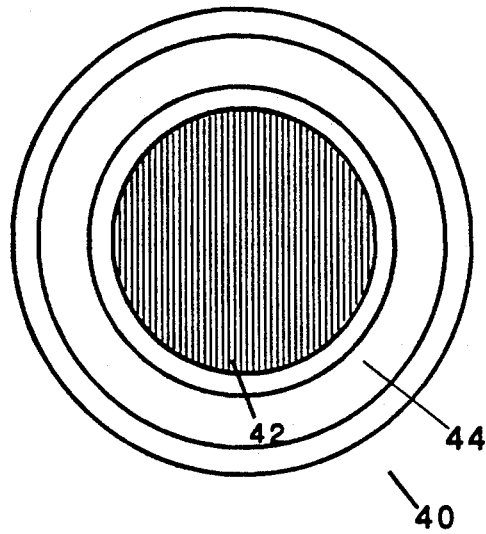

Referring to FIGS. 2A and 2B, active integrated monitor 40 has a replaceable coated filter 42, formed as described above, held within a container having an open face inlet 44 and a screw base 46. Filter 42 is replaced by unscrewing inlet 44 and base 46 and inserting a new filter between the inlet and base. A pump (not shown) is connected to pipe 48 to draw air (shown by arrow 50) through the filter.

Figure 4:
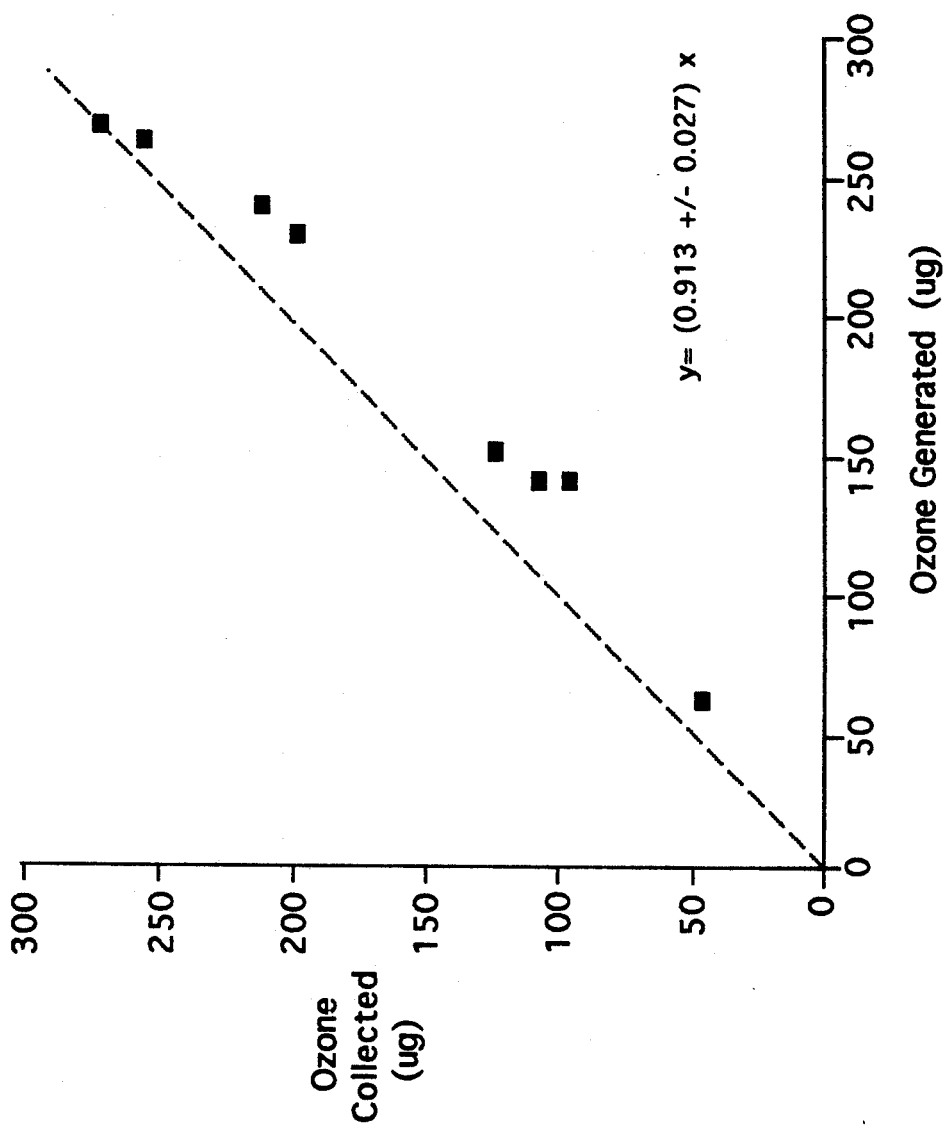
FIG. 4 is a graphical comparison of results obtained through laboratory experiments using an ozone monitor of the present invention and a UV analyzer.

The performance of the above active integrated ozone sampler was tested in both laboratory and field experiments. For the laboratory tests, known amounts of ozone, ranging between 50 and 300 μg, were generated using an ozone calibrator. Sampling periods varied between 1 and 12 hours. FIG. 4 compares measurements from the active sampler with a continuous UV-photometric ozone analyzer (manufactured by Thermo Environmental Instruments, Inc., Model 49 having a teflon filter in the input line to prevent particles from entering the monitor; calibrated using an ozone calibrator Model 49PS). The mass of ozone collected by the active sampler were slightly lower (approximately 9%), than those generated by the ozone calibrator. The results of these eight laboratory tests show good agreement between the integrated active sampler and the standard ozone monitor.

Figure 5:
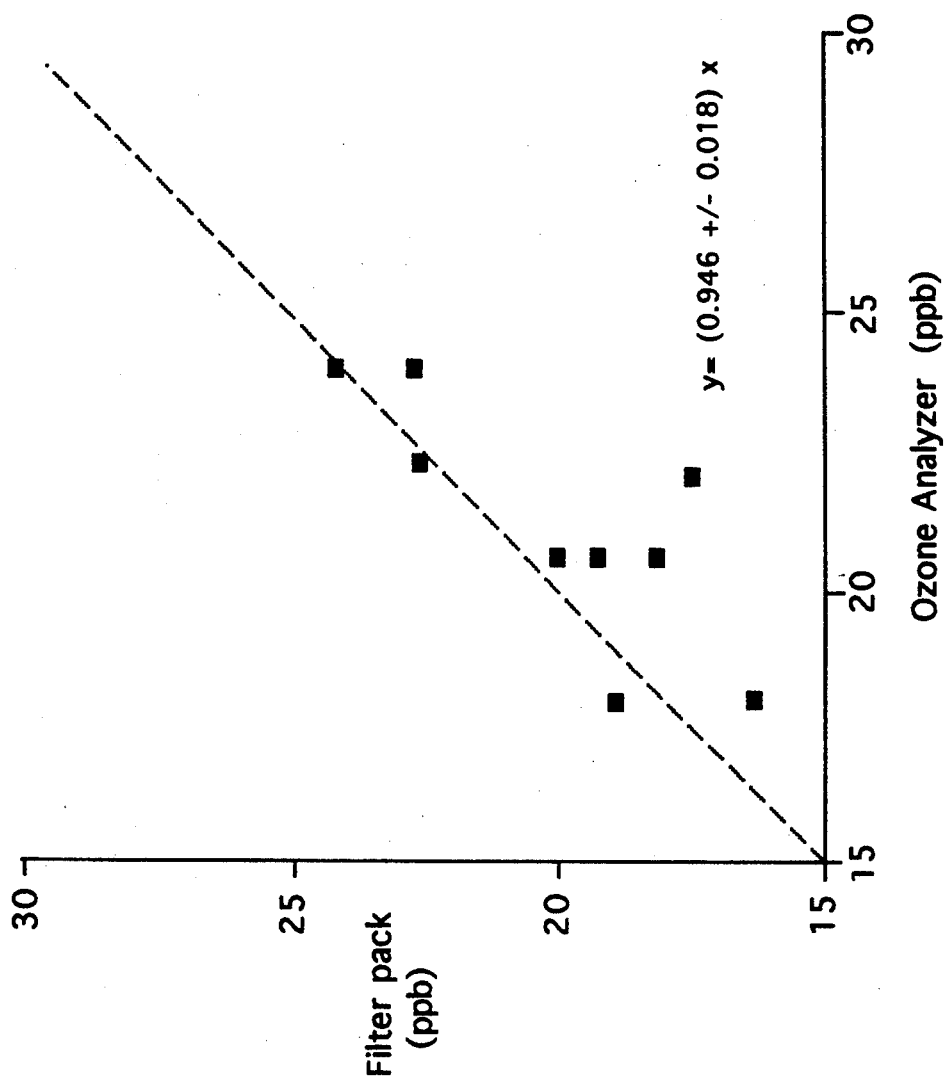
FIG. 5 is a graphical comparison of ozone determinations made in field experiments by a monitor of the present invention and a continuous ozone monitor.

In field tests, two active samplers were co-located with a UV-photometric continuous ozone analyzer. Sampling durations were approximately 24 hours. FIG. 5 compares the ozone concentrations obtained from the active samplers and a continuous ozone monitor. Again ozone measurements from the continuous instrument are slightly higher, by approximately 5%.

Figure 6:
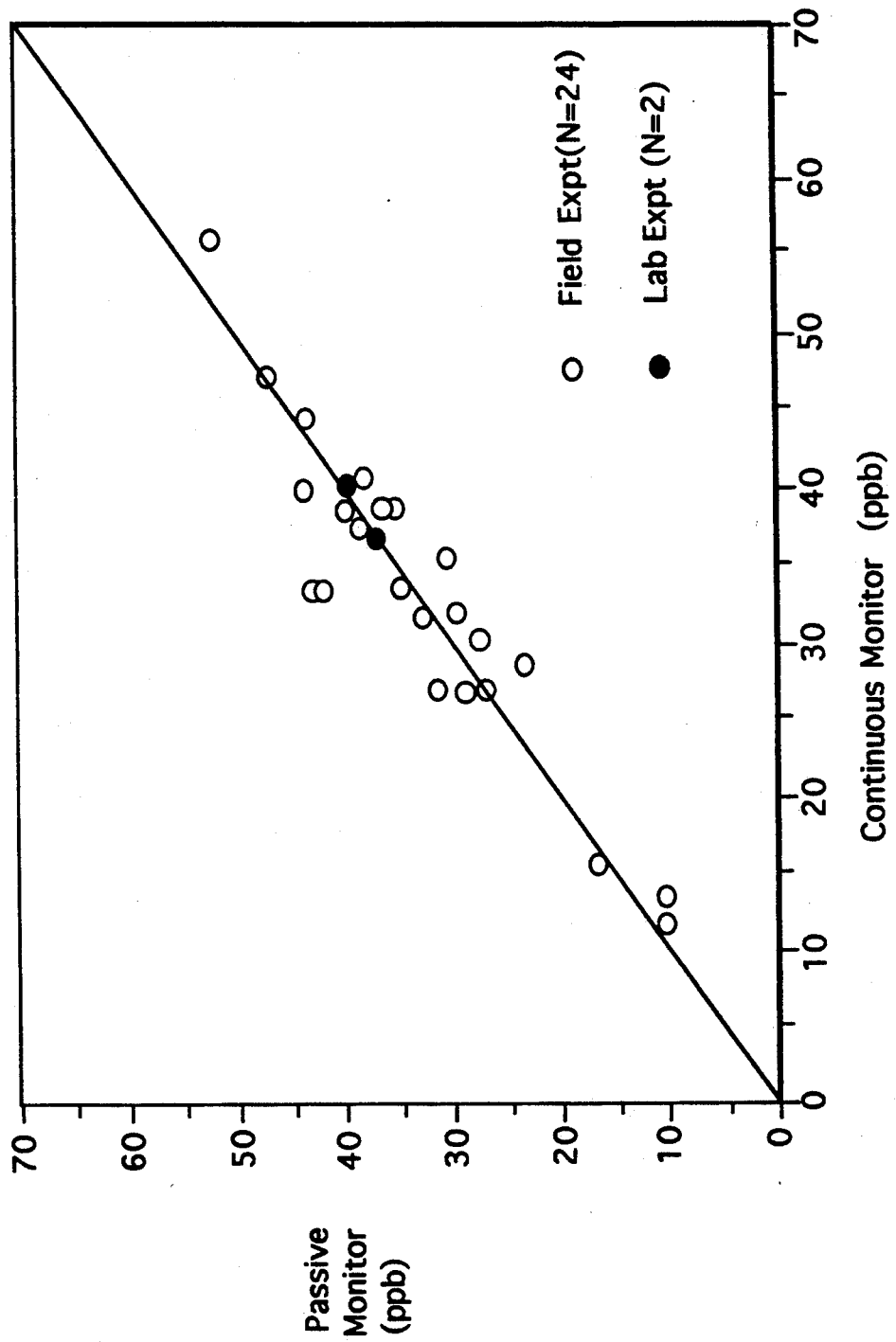
FIG. 6 is another graphical comparison of field experiments using an ozone monitor of the present invention and a UV analyzer.

FIG. 6 compares field and laboratory results obtained from passive samplers to a continuous UV-photometric ozone monitor. Good agreement is again found.

Further laboratory and outdoor experiments were conducted at the U.S. EPA laboratories at Research Triangle Park, N.C., during the period of Feb. 28 through Mar. 28, 1990. The results are shown in Table 1. For the laboratory experiments, the exposure time was 16 hours. Relative humidity varied between <10% and 60%. For one of the chamber experiments, nitrogen dioxide was mixed with ozone to investigate interference of this oxidant with ozone measurements. For all laboratory tests, as shown by Table 1, good agreement was found between the continuous UV analyzer and the above-described passive ozone sampler. The mean difference between the results obtained with these two devices was less than 10%. Furthermore, although only one outdoor experiment was conducted, the results of Table 1 show a good agreement between the two devices.

TABLE 1

| Results from evaluation tests conducted at the U.S. EPA | | | | | |
|---|---|---|---|---|---|
| Test Type | Relative Humidity | Exposure Time (min.) | UV analyzer ppb of O3 | New method ppb of O3 | Difference (%) |
| chamber | <10% | 960 | 125.0 | 117.0 | −6 |
| chamber | <10% | 960 | 37.0 | 31.5 | −15 |
| chamber | <10%* | 960 | 30.0 | 30.8 | +3 |
| chamber | 35% | 960 | 34.0 | 32.2 | −5 |
| chamber | 60% | 960 | 37.0 | 39.1 | +6 |
| chamber | <10% | 960 | 15.5 | 15.9 | +3 |
| chamber | <10% | 960 | 162.0 | 164.0 | +1 |
| chamber | <10% | 960 | 167.0 | 168.8 | +1 |
| chamber | <10% | 960 | 150.0 | 156.9 | +5 |
| outdoor | outdoor | 1260 | 31.0 | 28.3 | −9 |

*In the presence of 76 ppb of NO2.

OTHER EMBODIMENTS

Figure 3:
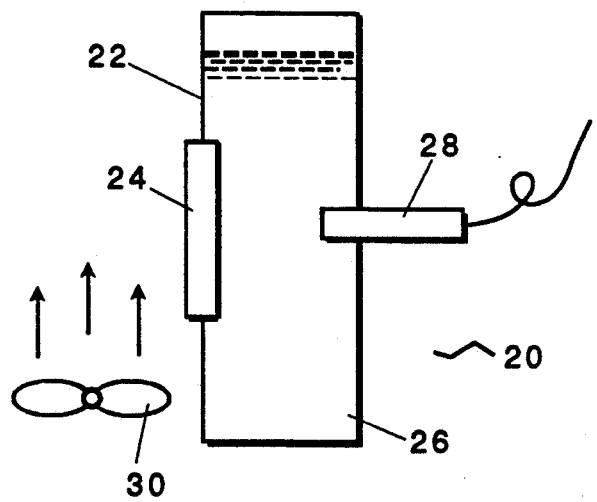
FIG. 3 is a diagrammatic cross-sectional view of a continuous ozone monitor.

Other embodiments are within the following claims. For example, referring to FIG. 3, a continuous ozone monitor 20 is formed from a closed container 22 having a membrane 24 which allows gas to enter liquid 26 within container 22 but does not allow liquid 26 to pass. Also provided is a nitrate electrode 28 which continuously monitors the nitrate concentration within liquid 26. Liquid 26 contain nitrite, carbonate and glycerol, as described above; as an ozone monitoring solution. Also provided is an optional fan 30 to cause air (shown by arrows) to be passed over membrane 24.

We claim:
1. An ozone monitor comprising:
an ozone reactive surface having a chemical coating comprising nitrite ions, a basic compound, and a hygroscopic component, said surface being constructed so as to specifically react with ozone, said surface also being constructed so as to fail to react with nitrogen dioxide in an amount which affects ozone quantitation by more than 20% when said nitrogen dioxide is provided at a concentration of 76 ppb and ozone is provided at a concentration of 30 ppb within a test gas; wherein said nitrite ions are reactive with ozone to form nitrate ions, wherein the quantity of said nitrate ions is indicative of the quantity of ozone monitored;

said surface being held within a container.

2. The ozone monitor of claim 1 wherein said surface is further constructed so s to allow quantitation of said ozone within a factor of 20% at humidities between 10% and 90%.

3. The ozone monitor of claim 1 wherein said hygroscopic component is glycerol.

4. The ozone monitor of claim 1 wherein said surface is further constructed so as to allow quantities of said ozone within a factor of 20% at temperatures between +50° F. and +100° F.

5. The ozone monitor of claim 4 wherein said surface is further constructed so as to allow quantitation of said ozone within a factor of 20% at humidities between 10% and 90%.

6. The ozone monitor of claim 1 wherein said coating comprises less than 0.003% by weight nitrate ions prior to exposure to ozone.

7. The ozone monitor of claim 6 wherein said nitrite ions are provided by sodium nitrite.

8. The ozone monitor of claim 6, further comprising a nitrate electrode positioned so as to detect said nitrate ions.

9. The ozone monitor of claim 1 wherein said basic compound is a carbonate.

10. The ozone monitor of claim 9 wherein said carbonate is potassium carbonate.

11. The ozone monitor of claim 1 wherein said surface is a liquid phase and said container is constructed so as to allow gaseous contact with said liquid.

12. The ozone monitor of claim 11 wherein said container comprises a membrane which allows gas to pass but not liquid to pass through said membranes.

13. The ozone monitor of claim 1 wherein said surface is a solid surface.

14. The ozone monitor of claim 13 wherein said surface is a filter and said container constructed so as to be located on a stationary object or on the outer clothing of a person.

15. The ozone monitor of claim 14 wherein said container envelops said filter and comprises openings to allow gas external to said monitor to pass through said openings to contact said filter.

16. The ozone monitor of claim 14 or 15 wherein said monitor is further provided with a fan or pump positioned so as to actively cause gas external to said monitor to contact said filter.

17. An ozone monitor comprising an ozone reactive surface comprising sodium nitrite, potassium carbonate, and glycerol wherein said nitrite ions are reactive with ozone to form nitrate ions, wherein the quantity of said nitrate ions is indicative of the quantity of ozone monitored.

* * * * *